US005700908A

United States Patent [19]
Ruoslahti

[11] Patent Number: 5,700,908
[45] Date of Patent: Dec. 23, 1997

[54] $\beta_3$ INTEGRIN CYTOPLASMIC DOMAIN SPECIFIC PEPTIDE AND NUCLEIC ACID

[75] Inventor: Erkki I. Ruoslahti, Rancho Santa Fe, Calif.

[73] Assignee: La Jolla Cancer Research Foundation, La Jolla, Calif.

[21] Appl. No.: 459,246

[22] Filed: Jun. 1, 1995

Related U.S. Application Data

[62] Division of Ser. No. 240,967, May 10, 1994, Pat. No. 5,498,694, which is a continuation of Ser. No. 973,547, Nov. 9, 1992, abandoned, which is a continuation of Ser. No. 357,024, May 25, 1989, abandoned.

[51] Int. Cl.⁶ .................. C07K 14/705; C07H 21/04
[52] U.S. Cl. .................. 530/324; 530/300; 530/350; 536/23.1; 536/23.5
[58] Field of Search .................. 530/324, 300, 530/350; 536/23.1, 23.5

[56] References Cited

U.S. PATENT DOCUMENTS 4,722,899  2/1988  Hamaoka et al. .................. 435/172.2
5,114,842  5/1992  Plow et al.

OTHER PUBLICATIONS

Fitzgerald et al. J Biol Chem 262: 3936–3939 (1987).
Zimrin et al. J Clin Invest 81: 1470–1475 (1988).
Coombs, *Dictionary of Biotechnology* Elsevier Science Pub. Co. Inc., New York, pp.312 and 120 (1986).
Harlow, et al., *Antibodies, A Laboratory Manual* Cold Spring Harbor Laboratory. p.98 (1988).
Rudinger, *Peptide Hormones*, Parsons (ad.) U. Park Press. Baltimore, pp. 1–7 (1976).

Marcantonio, E.E. and Hynes, R.O. "Antibodies to the Conserved Cytoplasmic Domain of the Integrin $\beta_1$ Subunit React with Proteins in Vertebrates, Invertebrates and Fungi." *The J. Cell Biol.* 106:1765–1772 (1988).
Ruoslahti, Erkki and Pierschbacher, Michael D. "New Perspective in Cell Adhesion: RGD and Integrins." *Science* 238:491–497 (1987).
Argraves et al., "Amino Acid Sequence of the Human Fibronectin Receptor." *J. Cell Biol.* 105:1183–1190 (1987).
Damsky, C.H. et al., "Distribution of the Cell Substratum Attachment (CSAT) Antigen on Myogenic and Fibroblastic Cells in Culture." *J. Cell Biol.* 100:1528–1539 (1985).
Chen, W. et al., "Development of Cell Surface Linkage Complexes in Cultured Fibroblasts." *J. Cell Biol.* 100:1103–1114 (1985).
Dejana E. et al., "Fibronectin and Vitronectin Regulate the Organization of Their Respective Arg–Gly–Asp Adhesion Receptors in Cultured Human Endothelial Cells." *J. Cell Biol.* 107:1215–1223 (1988).
Burn, P. et al., "Dynamic Membrane–Cytoskeletal Interactions: Specific Association of Integrin and Talin Arises In Vivo After Phorbol Ester Treatment of Peripheral Blood Lymphocytes." *Proc. Natl. Acad. Sci. USA* 85:497–501 (1988).
Seaver, Sally S. "Monoclonal Antibodies in Industry: More Difficult Than Originally Thought." *Genetic Engineering News*. pp. 10 and 21 (1994).

*Primary Examiner*—Lila Feisee
*Assistant Examiner*—Phillip Gambel
*Attorney, Agent, or Firm*—Campbell & Flores LLP

[57] ABSTRACT

The invention is directed to a peptide having the amino acid sequence of the cytoplasmic domain of integrin subunit $\beta_3$', KFEEERARAKWDTVRDGAGRFLKSLV, or subsequences thereof, and the nucleic acid encoding that peptide.

2 Claims, 3 Drawing Sheets

FIG. 3

```
2088  GTG GTA GAA GAG CCA GAG TGT CCC AAG GGC CCT GAC ATC CTG GTG CTG CTC TCA GTG β3'
       V   V   E   E   P   E   C   P   K   G   P   D   I   L   V   L   L   S   V
2148  ATG GGG GCC ATT CTG GCC GCC ATT GGC CTT GCC GCC CTC ATC CTG AAA CTC CTC ACC β3'
       M   G   A   I   L   A   A   I   G   L   A   A   L   I   L   K   L   L   T
2208  ATC CAC GAC CGA AAA GAA TTC GCT AAA TTT GAA GAA GAA CGA AGA GCC AGA AAA TGG GAC β3'
       I   H   D   R   K   E   F   A   K   F   E   E   E   R   A   R   A   K   W   D
2268  ACA GTA AGA GAC AAC AAC CCA CTG TAT AAA GAG GCT CTA TTT AAG TCA GAC ACG TAA GTG GAA β3'
       T   V   R   D   N   N   P   L   Y   K   E   A   L   F   K   S   D   T   *   V   E
       ACA GCC AAC CCA GCC CCA CCA CTG                                     TCT ATC ATC ACG
        T   A   N   P   A   P   P   L                                      S   I   I   T
2328  GCA GCA
       A   A
       GGC ACT  GAT GCT TTG GGT GGT GTC CAG GTT CAT ATC TCT TTC CAT TAT CCT CTG β3'
        G   T   D   A   L   G   G   V   Q   V   H   I   S   F   H   Y   P   L
              TAA TGA GCT TAA TAA GCA ATC TCG CTC TGT GCC TCA GCT TTT GTA GTA
                *       A        A    I   S   L   C   A   S   A   F   V   V
2388  TTC GTC AAA CTG ATC GGA GAG TTT ATG ACA TGT TGT CCT TGT GGG CCT TGT TCA AGC CTC β3'
        F   V   K   L   I   G   E   F   M   T   C   C   P   C   G   P   C   S   S   L
              AAT GCC ATC AGG GCA GAA CAT CAG TGT CAG CCA TCA TCG GGA GAG TCA
2448  TTA GAA ATA GTG TTG GCA GGA CCA TGT CAT AGG GAG TTT ATC TCC TAT TCC TGT β3'
        L   E   I   V   L   A   G   P   C   H   R   E   F   I   S   Y   S   C
              AGG GGT TTG CAC GCA CTG GCA CCA CAG GGT GTT CTT CGC TTG ATC GTG GAT
2508  TTA GTC CTT CTG GCC CGC AGT CCT GGC GTG GTA GCC AAT GCC CCA GTA GCA CTT TTA β3'
        L   V   L   L   A   R   S   P   G   V   V   A   N   A   P   V   A   L   L
              GGT TGT CCA TGT TAT AGG GCC GTG ACT CGG AGG GAT TGA AAA ACA TGC
2568  GTG GTC AGA TCA CTT CTG TGG TGT AAG AGT CCT GCA GCA TCC AAT TGG AGG GAT TGA AAA ACA TGC β3'
        V   V   R   S   L   L   W   C   K   S   P   A   A   S   N   W   R   D   *   K   T   C
2628  GTC TGC AGA ATA ATT AAT AGC TGC ATA ATT AGG GGA CCA TGG GTT CTT TGC TGG TGC β3'
       V   C   R   I   I   N   S   C   I   I   R   G   P   W   V   L   C   W   C
2688  ATT CGG GAG GCT TTC CCC AGG GGA BCA GGA TTG GAT AGT CAG GCA CCC ATG CAT TAG ATC CCT GTA ATC CCA GCT β3'
2748  GAG CCA GCA GAA TGG ACA AGC CTT TCT GGG TGA CAG CTT TAC GCT TTC GGC CAA TTG AGG CTG AGA AGC CTC TTC GTC TAA TAA ATC TAT GGT β3'
2808  TAA TAA AAT CTC TAA CTC TCA AAT GCT ATA AAA GGA CTG TAT GAA TAA GTC AAG CGG AAA CGG AAA TGT AAA ACC AAA ACC β3'
2868  AAA AAA AAA AAA AAA AAA AAA AAA AAA AAA AAA AAA AAA AAA AAA AAA AAA AAA AAA AAA AAA
       AAA TCT GCC TCC GCC TTT CCC GCA GGA AAA CTC CCT CAG GTC ATC CGG TGA AGC CTC AGG GGA AGC AGC GAG AGC ATT AGA
```

β₃ INTEGRIN CYTOPLASMIC DOMAIN SPECIFIC PEPTIDE AND NUCLEIC ACID

This application is a divisional of application Ser. No. 08/240,967, filed May 10, 1994, now U.S. Pat. No. 5,498,694 which is a continuation of application Ser. No. 07/973,547, filed Nov. 9, 1992, now abandoned, which is a continuation of application Ser. No. 07/357,024, filed May 25, 1989, now abandoned.

BACKGROUND OF THE INVENTION

Integrins are a family of adhesion receptors (reviewed in Ruoslahti and Pierschbacher, Science, 238:491–497, 1987). An integrin molecule is a heterodimeric membrane protein composed of one α subunit and one β subunit. Several subunits of each kind are known, and various combinations of these subunits make up receptors with different ligand specificities. The ligands for integrins are extracellular matrix proteins such as fibronectin, laminin, collagens and vitronectin or membrane proteins at the surface of other cells.

By binding to their ligands, integrins mediate the adhesion of cells to extracellular matrices and other cells. Adhesion is important for a cell. It provides anchorage, traction for migration, signals for homing, and regulates growth and differentiation of cells.

There are a number of instances where it is important to determine the complement of adhesion receptors possessed by cells. For example, it has been shown that inhibition of the fibronectin receptor function by synthetic peptides that bind to this receptor prevents tumor cells (Gehlsen et al., J. Cell. Biol., 106:925–930, 1988) or lymphocytes (Thiery et al., Ann. Rev. Cell. Biol., 1:91–113, 1985) from invading and migrating through tissues. In contrast, inhibition of the function of another integrin, the vitronectin receptor, has no effect on tumor cell migration (Gehlsen et al., op cit.). Thus, it would be important to determine whether a tumor has fibronectin receptors to assess the potential susceptibility of its invasive properties to inhibitors of this receptor. Similar considerations apply to the laminin receptors, which are also thought to play a role in invasion (Gehlsen et al., Science 241:1228–1229, 1988).

Another situation in which determination of the integrins possessed by cells is important, is when the tissue of origin of a tumor is analyzed. Tissue-specific markers have proven to be a very useful adjunct for such an analysis in the clinical pathology setting. Some of the integrins are tissue-specific in their expression, providing potentially useful markers for the diagnosis of tumor origin. Thus, for example, the primary platelet integrin gp IIb/IIIa is restricted to platelets and leukemia cells capable of expressing megakaryocytic properties (in BIOCHEMISTRY OF PLATELETS, D. R. Phillips and M. A. Schuman, Eds., Academic Press, N.Y., 1986; Suzuki et al., J. Biol. Chem. 262:14080–14085, 1987). As is the case with most other cellular markers, the detection of integrins in cells and tissues is best accomplished with antibodies.

There thus exists a need for antibodies specific to various integrins. This invention satisfies this need by providing a simple and reproducible method for the preparation of anti-integrin antibodies suitable for the detection and quantitation of integrins by immunoassays.

SUMMARY OF THE INVENTION

The present invention provides anti-integrin antibodies produced by immunizing with peptides derived from the cytoplasmic domains of integrin subunits. The α and β integrin subunits each have a short cytoplasmic tail that can be entirely, or in part, reproduced as synthetic peptides. Particular peptide sequences useful for such immunization, including a variant β₃' peptide, are also provided.

BRIEF DESCRIPTION OF DRAWINGS

FIG. 3 shows the cDNA sequence and deduced amino acid sequence of the cytoplasmic domain of the β₃' subunit. The sequence of the EcoRI fragment containing the alternative cytoplasmic domain is shown and referred to as β₃'. Part of the published β₃ sequence is shown for comparison. Amino acids are indicated in single-letter code. The putative transmembrane domain in the β₃ sequence is boxed. The site where the two sequences become different is indicated by an arrow. Polyadenylation signals are underlined.

DETAILED DESCRIPTION OF THE INVENTION

Figure 1:
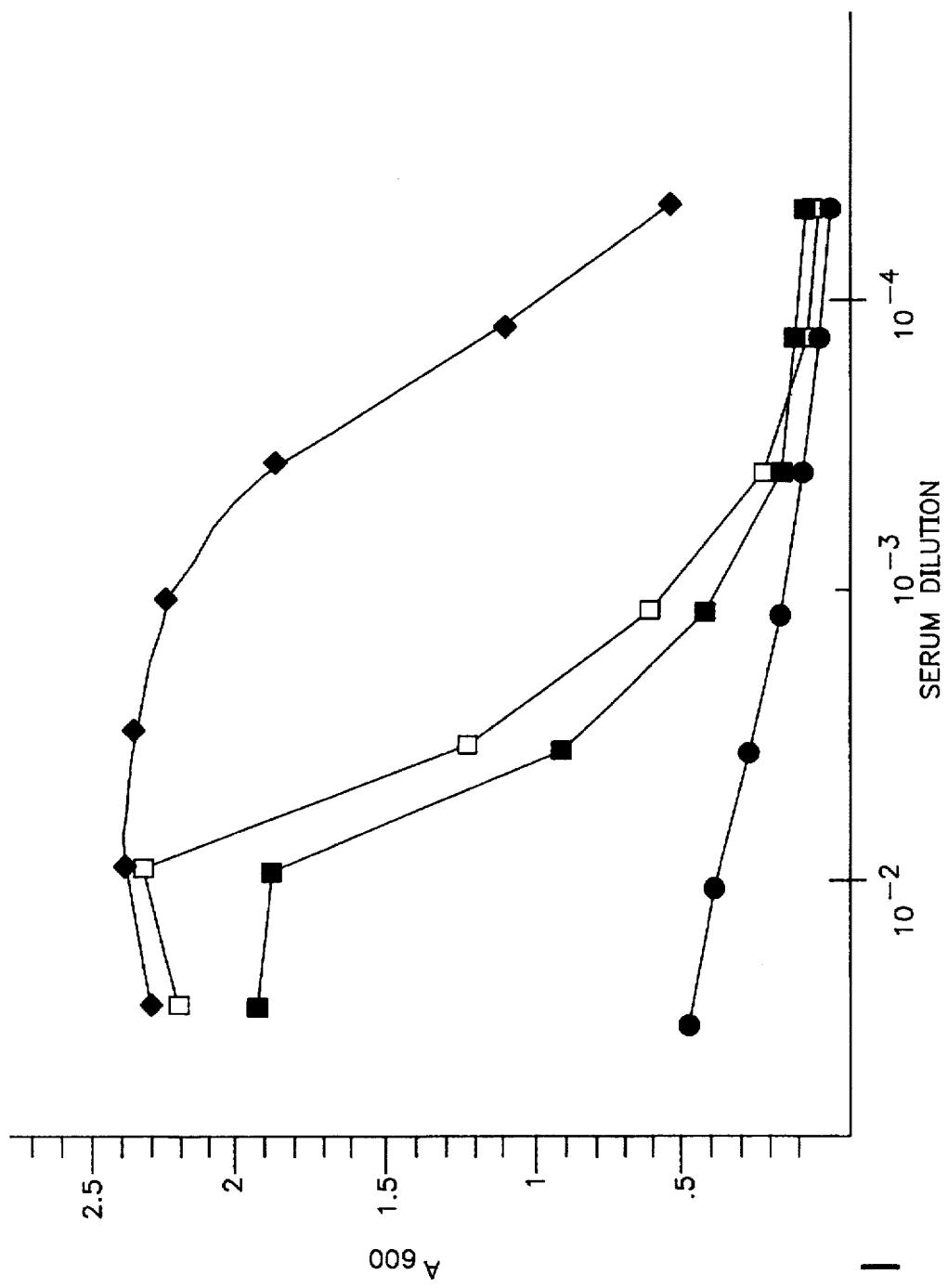
FIG. 1 shows the reactivity of antisera prepared against the cytoplasmic domains of the α₅ and β₁ subunit with the fibronectin receptor (α₅β₁) in ELISA. Microtiter wells were coated by incubation with purified human placental fibronectin receptor (10 μg/ml in Tris buffered saline, pH 7.4, containing 5 mM β-octylglucopyranoside). Residual binding sites on the plastic were saturated by post-coating with phosphate buffered saline containing 0.25% BSA. The wells were then incubated with the indicated dilutions of the following sera: (●) preimmune serum, (■) antiserum against β₁ cytoplasmic peptide (after second injection of the antigen), (□) antiserum against β₁ cytoplasmic peptide (after third injection of the antigen), (♦) antiserum against α₅ cytoplasmic peptide (after the fourth injection of the antigen). Bound antibodies were detected with alkaline phosphatase conjugated goat anti-rabbit IgG (Cappel Laboratories, Malvern, Pa). The color reaction was quantitated by light absorbance at 600 nM.

The present invention relates to antibodies prepared against integrins. These antibodies are characterized by their having been elicited by immunizing with synthetic peptides corresponding to the cytoplasmic domains or portions thereof of various integrin subunits. The amino acid sequences of several integrin subunits are available (Tamkun et al., Cell 42:271–282, 1986; Argraves et al., J. Cell Biol. 105:1183–1190, 1987; Suzuki et J. Biol. Chem. 262:14080–14085, 1987; Poncz et al., J. Biol. Chem. 262:8476–8482, 1987; Fitzgerald et al., J. Biol. Chem. 262:3936–3939, 1987; Fitzgerald et al., Biochemistry 26:8158–8165, 1987; DeSimone and Hynes, J. Biol. Chem. 263:5333–5340, 1988; Kishimoto et al., Cell 48:681–690, 1987; Law et al., EMBO J. 6:915–919, 1987; Pytela, R., EMBO J. 7:1371–1378, 1988 all of which are incorporated herein by reference).

Immunization with such peptides has two distinct advantages: the immunization is performed with a synthetic peptide corresponding to the end of the natural polypeptide, and the synthetic peptide corresponds to an intracellular peptide domain. Peptides from either end of a protein have been found to be more likely to be immunogenic than ones derived from internal sequences in the same protein (Harlow and Lane, ANTIBODIES: A LABORATORY MANUAL, Cold Spring Harbor, 1988) and it was felt that antibody production to intracellular proteins (or cytoplasmic portions of transmembrane proteins) is less likely to be hampered by tolerance than production of antibodies to proteins that exist extracellularly. For these reasons, and because the various integrin subunits differ in their cytoplasmic sequences, peptides from the cytoplasmic domains were considered good candidates for the use of immunogens in the production of antibodies against integrins. However, the results were unexpectedly good in that unusually potent antisera reactive with the appropriate integrin were obtained in each case.

The peptides listed in Table I, which are based on known cytoplasmic domain amino acid sequences from integrin subunits, were synthesized using the Applied Biosystems, Inc. model 430A automatic peptide synthesizer and the chemistry provided by the manufacturer. In some cases the peptide was synthesized with a cysteine added at the $NH_2$-terminus to facilitate coupling to carrier protein. The cysteine-containing peptides were coupled to keyhole limpet hemocyanin (KLH) by using m-maleimidobenzoyl-N-hydroxysuccinimide ester (Pierce Chemical Co., Rockford, Ill. according to O'Sullivan et al. (Analyt. Biochem. 100::100–108, 1979) which is incorporated herein by reference. The peptides with no added cysteine were similarly coupled to KLH by using N-succinimidyl 3-(2-pyridyldithio) propionate (Pharmacia Fine Chemicals, Piscataway, N.J.) according to the manufacturer's instructions. The resulting conjugates were emulsified in Freund's complete adjuvant and injected into rabbits. Further injections of conjugate in Freund's incomplete adjuvant were given after one, two and three months. The dose of each injection was equivalent to 0.6 mg of peptide. Blood was collected 10 days after the third and fourth injection. The antisera were tested against the glutaraldehyde-cross linked peptides and isolated receptors in ELISA (Engvall, Meth. Enzymol. 70:419–439, 1980), in immunoprecipitation and immunoblotting, and by staining cells in immunofluorescence, as is well known in the art. The results show that the antisera specific for the individual integrins have been obtained.

TABLE I

| $NH_2$ | COOH |
|---|---|
| $\beta_1$ | EFAKFEKEKMNAKWDTGENPIYKSAVTTVVNPKYEGK |
| $\beta_3$ | KFEEERARAKWDTANNPLYKEATSTFTNITYRGT |
| $\beta_3$' | KWDTVRDGAGRFLKSLV |
| $\alpha_5$ | CEKAQLKPPATSDA |
| $\alpha_v$ | KRVRPPQEEQEREQLQPHENGEGNSET |

Amino acids are designated by their standard one letter abbreviation.

EXAMPLE I

Identification of a novel cytoplasmic sequence for integrin subunit $\beta_3$

A CDNA clone that encodes a $\beta_3$ variant, termed $\beta_3$', with a new cytoplasmic domain sequence was identified. This cytoplasmic domain was used to generate one of the antisera of this invention. cDNA clones were isolated from λgt 11 cDNA libraries made from myeloma cell RNA by use of a cDNA cloning kit (Amersham, Arlington, Ill.) and from placental RNA (Millan, J. Biol. Chem. 261:3112–3115 1986). A 21-mer oligonucleotide, 5' CAC TGA GAG CAG GAC CAC CAG 3', from the published sequence of $\beta_3$ (Rosa et al., Blood 72:593–600, 1988 and Fitzgerald et al., Supra) or inserts from cDNA clones were used for the screening.

Screening of $3\times10^5$ plaques from a M 21 myeloma cDNA library with a 21-mer oligonucleotide probe from the published $\beta_3$ cDNA sequence revealed one positive clone. The 1.3 kb cDNA insert from this clone was used to screen $7\times10^5$ plaques from a placental λgt 11 cDNA library, resulting in the isolation of three positive clones. The inserts of the isolated cDNA clones were subcloned into the phage vector M13 mp19 as is well known in the art and sequenced by the dideoxy chain termination method either manually with dATP 5'-α-[$^{35}S$] thiotriphosphate as the label or by using an automated DNA-sequencer and fluorescent primers (Applied Biosystems, Foster City, Calif.; model 370A) according to the manufacturer's instructions.

Partial sequences of two of the clones revealed the same sequence as in the published $\beta_3$ sequence. Unexpectedly, the third clone (#10) was different. This 1.8 kb clone consisted of 1.0 and 0.8 kb EcoRI fragments, and its 5' end is in the extracellular domain (base number 1254; sequence numbers are according to Rosa et al., Blood 72:593–600 (1988). The published $\beta_3$ sequence and the clone 10 sequence were found to be identical through the 5' fragment and part of the 3' fragment but diverged within the 3' fragment in the region that encodes the cytoplasmic domain of the $\beta_3$ polypeptide. The DNA sequence of the 3' fragment and the amino acid sequence derived from it are shown in FIG. 3. The variant sequence encodes a cytoplasmic domain in which the COOH-terminal 21 amino acids of the previously known $\beta_3$ sequence have been replaced with a new 13-amino acid sequence. (See Table 1.) The identity of most of the $\beta_3$' cDNA sequence with the known $\beta_3$ sequence and the fact that these two sequences diverge near the usual splice site dinucleotide GT provide a strong indication that the $\beta_3$ and $\beta_3$' mRNAs arise from the same gene by alternative splicing.

The existence of a cDNA clone containing the $\beta_3$' suggests that the $\beta_3$' is expressed at least at the mRNA level. Further proof for the existence of such a cDNA was obtained by applying the reverse transcriptase-polymerase chain reaction method (RT-PCR, Rappolee et al., Science 241:708–712 (1988) which is incorporated herein by reference). RNA was isolated from MG-63 human osteosarcoma cells (American Type Culture Collection) and from human placental tissue by using the guanidine isothiocyanate method and used to generate DNA fragments from $\beta_3$ and $\beta_3$' mRNA by RT-PCR.

RT-PCR was essentially done as described Rappolee, Supra. Total RNA (0.4 µg) was reverse transcribed using 200 U of Moloney murine leukemia virus reverse transcriptase (Bethesda Research Laboratories, Gaithersburg, Md.), 0.4 µg oligo p(dT) 12–18 and 2 µg nuclease-free bovine serum albumin. The total volume was 20 µl. One-tenth of the resulting cDNA was amplified by using the DNA amplification reagent kit and thermal cycler (Perkin-Elmer Cetus, Norwalk, Conn.). One unit of Taq polymerase and 1 µM of each primer were used; the final volume was 50 µl. The following primers were used: #1—extracellular domain 1851–1875; #2—extracellular domain 1879–1903; #3—extracellular domain 2064–2088; #4—cytoplasmic domain $\beta_3$ 2273–2297; #5—3' untranslated region $\beta_3$ 2559–2583; #6—3' untranslated region $\beta_3$ 3104–3128;

7—3' untranslated region β 3472–3497; #8—cytoplasmic domain+3' untranslated region alternative sequence 2301'–2331' (the ' symbol refers to the variant β sequence); #9 - 3' untranslated region alternative sequence 2408'–2432'. Of the PCR mixture, 15 µl were electrophoretically separated in 2% agarose gels or 3% NU SIEVE GTG/1% SAEKEM GTG agarose gels (FMC, Rockland, Me.) and DNA was visualized using ethidium bromide. Hae III fragments of ΦX174 RF DNA (500 ng) were used as molecular size markers (Bethesda Research Laboratories, Gaithersburg, Md.). RNA digestion was performed using 50 µg ribonuclease A (Sigma, St. Louis, Mo.) and 14 µg total RNA in a total volume of 30 µl. Digestion was for 20 hours at 37° C.

Analysis of the DNA fragments generated by the RT-PCR showed that a fragment of the expected size was obtained in each case both when the primers came from the $\beta_3$ sequence and when they came from the $\beta_3'$ sequence. Controls showed that the production of these fragments in the reaction was sensitive to digestion of the template MG-63 cell and placental RNA with RNAse prior to the RT-PCR. These results show that the $\beta_3'$ mRNA is expressed in the 63 cells and in the placenta. To provide a reagent for the detection of $\beta_3'$ at the protein level, a peptide was made from the cytoplasmic tail of $\beta_3'$(Table 1) and used to generate an antiserum.

EXAMPLE II

Reactivity of anti-integrin antisera in ELISA

A total of 5 antisera were prepared against the cytoplasmic domains of 5 different integrin subunits. Each immunization yielded an antiserum reactive with the immunizing peptide. All antisera were also reactive with the receptor proteins from which the peptide sequence was taken when tested in ELISA against the receptor. The $\beta_3'$ antiserum reacted also with the $\beta_3$ peptide which shares the sequence KWDT with the $\beta_3'$ peptide. It could be made specific for the $\beta_3'$ peptide by absorption with the $\beta_3$ peptide coupled to cyanogen bromide-activated SEPHAROSE (Pharmacia). After the absorption, the antiserum reacted only with the $\beta_3'$ peptide. It continued to react with the isolated vitronectin receptor suggesting that this receptor contains molecules with the sequence in addition to those representing $\beta_3$.

FIG. 1 shows an example of an ELISA titration curve with a number of bleedings from rabbits immunized with the cytoplasmic domains of the $\alpha_5$ and $\beta_1$ integrin subunits. It can be seen that specific reactivity against the purified intact receptor is present in each of the bleedings taken after the immunization, and that the amount of the antibody in the antiserum increases (as indicated by the highest dilution that shows binding of the receptor) as the immunization progresses.

Figure 2:
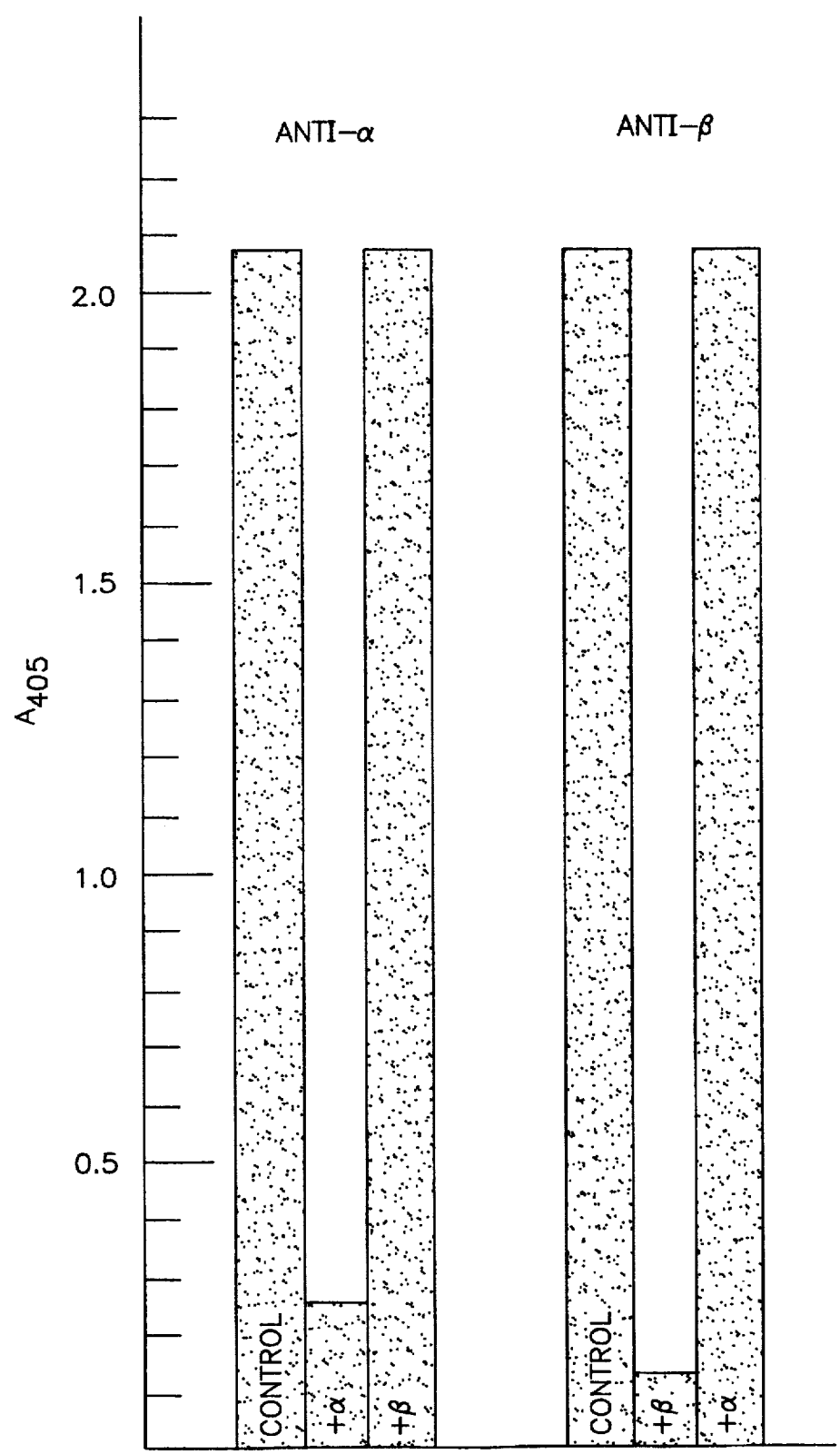
FIG. 2 demonstrates the specificity of cytoplasmic domain antisera by peptide inhibition in ELISA. Microtiter wells were coated with a solution containing 3 μg/ml of purified vitronectin receptor. Antisera prepared against peptides from the cytoplasmic domains of the vitronectin receptor α and β subunits diluted 1:1000 were incubated in the wells without added peptide (control) or with the indicated peptide at a concentration of 10 μg/ml. The binding of the antibodies to the wells was detected with alkaline phosphatase-conjugated anti-rabbit IgG (Cappel Laboratories, Malvern, Pa.).

FIG. 2 shows an example of the specificity of the cytoplasmic domain antisera. In this case antisera to the vitronectin receptor α and β subunits ($\alpha_v$ and $\beta_3$ in the nomenclature proposed by Hynes (Cell 48:549–554, 1987) were allowed to bind to wells coated with the vitronectin receptor and inhibition of the binding by peptides was studied. The results show that the binding of the anti-$\alpha_v$ subunit antiserum to the receptor was inhibited by the immunizing ($\alpha_v$) peptide but not by the peptide that came from the $\beta_3$ subunit. The opposite was true of the anti-$\beta_3$ subunit antiserum.

EXAMPLE III

Specificity of anti-integrin antisera in immunoblotting and immunoprecipitation

Immunoblotting showed that the anti-cytoplasmic peptide antisera bound to the integrin subunit from which the immunizing peptide was derived from.

The antisera were also reactive with integrins in solution as shown by immunoprecipitation. SDS-polyacrylamide gel electrophoresis analysis of material immunoprecipitated from surface-iodinated (Lebien et al., J. Immunol. 129:2287–2292, 1987 incorporated herein by reference) Chinese hamster ovary (CHO) cells (Urlaub and Chasin, Proc. Natl. Acad. Sci., USA 77:4216–4220, 1980) by antisera against the $\alpha_1$ and $\beta_1$ integrin subunits revealed two radioactive polypeptides the mobility of which corresponded to the $\alpha_5$ and $\beta_1$ subunits. No other detectable bands were present. Normal rabbit serum did not precipitate detectable bands. These results show that the antisera specifically recognize the appropriate integrin among all the various proteins that became labeled in the CHO cells.

EXAMPLE IV

Detection of receptors in cells by immunofluorescence

The anti-cytoplasmic domain antisera can be used to detect the presence of integrins in cell membranes. For example, an antiserum prepared against the $\alpha_5$ and $\beta_1$ subunit cytoplasmic domains was used to stain cultured CHO cells by immunofluorescence. Patchy staining was seen with both antisera, indicating that both subunits are present in the CHO cells and that the integrins containing these subunits are localized in specialized adhesion structures at the cell surface. The immunizing peptide inhibits the staining and no staining was obtained with preimmune control sera.

Although the invention has been described with reference to the presently-preferred embodiments, it should be understood that various modifications can be made without departing from the spirit of the invention. Accordingly, the invention is limited only by the following claims.

We claim:

1. A peptide having the amino acid sequence of the cytoplasmic domain of integrin subunit $\beta_3'$, KFEEERARAKWDTVRDGAGRFLKSLV.

2. A nucleic acid encoding a peptide having the amino acid sequence of the cytoplasmic domain of integrin subunit $\beta_3'$, KFEEERARAKWDTVRDGAGRFLKSLV.

* * * * *